United States Patent
Uchiyama

(10) Patent No.: US 8,314,622 B2
(45) Date of Patent: Nov. 20, 2012

(54) METHOD AND APPARATUS FOR EXAMINING ION-CONDUCTIVE ELECTROLYTE MEMBRANE

(75) Inventor: Naoki Uchiyama, Hamamatsu (JP)

(73) Assignee: Kabushiki Kaisha Asumitec, Shizuoka (JP)

( * ) Notice: Subject to any disclaimer, the term of this patent is extended or adjusted under 35 U.S.C. 154(b) by 352 days.

(21) Appl. No.: 12/668,231

(22) PCT Filed: Jul. 3, 2008

(86) PCT No.: PCT/JP2008/062096
§ 371 (c)(1),
(2), (4) Date: Jan. 8, 2010

(87) PCT Pub. No.: WO2009/008334
PCT Pub. Date: Jan. 15, 2009

(65) Prior Publication Data
US 2011/0001500 A1 Jan. 6, 2011

(30) Foreign Application Priority Data
Jul. 9, 2007 (JP) .................. 2007-179606

(51) Int. Cl.
*G01R 27/08* (2006.01)
(52) U.S. Cl. .......................... 324/718; 702/35
(58) Field of Classification Search .......... 324/432, 324/718, 456; 702/35; 73/45; 204/520, 204/518, 415, 400, 416, 640, 627; 429/482, 429/483, 400; 156/64
See application file for complete search history.

(56) References Cited

U.S. PATENT DOCUMENTS

| | | | |
|---|---|---|---|
| 2003/0170520 A1* | 9/2003 | Fujii et al. | 429/32 |
| 2004/0197633 A1* | 10/2004 | Yamamoto et al. | 429/34 |
| 2009/0108856 A1* | 4/2009 | Yonushonis et al. | 324/718 |

FOREIGN PATENT DOCUMENTS

| | | |
|---|---|---|
| JP | 2001-23665 | 1/2001 |
| JP | 2004-214089 | 7/2004 |
| JP | 2004-233097 | 8/2004 |
| JP | 2005-201822 | 7/2005 |
| JP | 2007-311191 | 11/2007 |
| JP | 2007-311193 | 11/2007 |

* cited by examiner

*Primary Examiner* — Jermele M Hollington
*Assistant Examiner* — Alesa Allgood
(74) *Attorney, Agent, or Firm* — Cozen O'Connor

(57) ABSTRACT

A detection membrane (11) is joined to a first surface (10a) of an electrolyte membrane (10), and hydrogen gas is supplied to a second surface (10b) thereof. If the electrolyte membrane has a defect (10c), hydrogen gas leaks to the first surface, resulting in a change in electric resistance of the detection membrane near the defect. The defect is recognized by this change. FA hydrogen electrode (14) is joined to the second surface, and an electric circuit (17) is connected between the detection membrane and the hydrogen electrode. Hydrogen gas supplied to a space facing the hydrogen electrode is ionized at the hydrogen electrode, and hydrogen ions permeates through the electrolyte membrane and hydrogenates the detection membrane. Whether or not hydrogen ion conductivity is uniform is examined by measuring electric resistance of the detection membrane, which varies depending on the amount of hydrogen ions, for each of regions.

13 Claims, 7 Drawing Sheets

METHOD AND APPARATUS FOR EXAMINING ION-CONDUCTIVE ELECTROLYTE MEMBRANE

RELATED APPLICATIONS

This is a U.S. National Phase Application under 35 USC §371 of International Application PCT/JP2008/062096 filed on Jul. 3, 2008.

This application claims the priority of Japanese Patent Application No. 2007-179606 filed Jul. 9, 2007, the entire content of which is hereby incorporated by reference.

TECHNICAL FIELD

The present invention relates to a method and apparatus for examining an ion-conductive electrolyte membrane.

BACKGROUND ART

An ion-conductive electrolyte membrane (hereinafter, sometimes referred to simply as "electrolyte membrane") is used in a fuel cell, for example, and a hydrogen ion-conducive membrane conducting hydrogen ions is used in a membrane electrode assembly of a solid polymer fuel cell, for example. Such membrane electrode assembly is constructed by joining a hydrogen electrode (fuel electrode) to one side of a solid polymer membrane which is an electrolyte membrane, and an air electrode (oxygen electrode) to the other side. In the solid polymer fuel cell having such membrane electrode assembly, hydrogen is supplied to the hydrogen electrode while oxygen (or air) is supplied to the air electrode. At the hydrogen electrode, hydrogen is ionized, namely split into hydrogen ions and electrons. The hydrogen ions permeate through the electrolyte membrane to reach the air electrode. The electrons produced at the hydrogen electrode travel through an electric load, connected between the hydrogen electrode and the air electrode, to the air electrode, and thus, electric power is supplied to the electric load. At the air electrode supplied with the electrons, hydrogen ions react with oxygen to form water (water vapor).

In such solid polymer fuel cell, if the electrolyte membrane has a defect, such as a pin hole or a crack, gas leaks through the defect, resulting in a reduction in electric power generation capacity. If hydrogen gas is supplied to a space facing one side of the electrolyte membrane, such defect allows the hydrogen gas to leak through it to the other side of the electrolyte membrane. Thus, the presence of a defect can be detected by measuring the concentration of leaked hydrogen gas with a hydrogen sensor. The hydrogen sensor for use in such measurement can be formed using a hydrogen-storing alloy, for example, as disclosed in Unexamined Japanese Patent Publication No. 2004-233097, for example.

In a solid polymer fuel cell having a plurality of membrane electrode assemblies electrically connected in series to increase output voltage, maximum output current is determined by the membrane electrode assembly lowest in hydrogen ion (proton) conductivity. It is therefore desirable that the membrane electrode assemblies connected in series be as uniform in hydrogen ion conductivity as possible. Thus, a method for producing membrane electrode assemblies uniform in hydrogen ion conductivity has been developed, as disclosed in Unexamined Japanese Patent Publication No. 2006-252938, for example.

In the examination method by detecting leaked hydrogen gas diffused in an atmosphere, an ability for detecting a defect of the electrolyte membrane lowers due to the diffusion of leaked hydrogen gas. In addition, detection of leaked hydrogen gas in an atmosphere does not give the location of the defect.

The method for producing electrolyte membranes and membrane electrode assemblies uniform in hydrogen ion conductivity is not a method for examining a produced electrolyte membrane on hydrogen ion conductivity; It cannot examine whether or not an electrolyte membrane has a proper level of uniformity with respect to the hydrogen ion conductivity.

DISCLOSURE OF THE INVENTION

The present invention has been made in view of the problems as mentioned above. The primary object of the present invention is to provide an examination method and apparatus capable of more accurately examining an ion-conductive electrolyte membrane.

In order to achieve the above object, in a method for examining an ion-conductive electrolyte membrane according to the present invention, a detection membrane including a thin film layer is joined to a first surface of the ion-conductive electrolyte membrane, and hydrogen gas is supplied to a space facing a second surface of the ion-conductive electrolyte membrane. If the ion-conductive electrolyte membrane has a defect, hydrogen gas leaks from the second surface to the first surface of the ion-conductive electrolyte membrane through the defect, so that the thin film layer is hydrogenated in a portion near the defect and varies in electric resistance. Thus, whether or not a defect exists can be examined quickly with high accuracy by examining whether or not the thin film layer has undergone a change in electric resistance owing to hydrogenation.

If, for example, the thin film layer is provided for each of a plurality of regions into which the first surface of the ion-conductive electrolyte membrane is divided, the thin film layer corresponding to a region having a defect is hydrogenated by leaked hydrogen gas and varies in electric resistance. Thus, in this case, the region having a defect can be identified by measuring the electric resistance of each of the thin film layers provided for the respective regions to detect a thin film layer having undergone a change in electric resistance.

Gas pressure in the space facing the second surface of the ion-conductive electrolyte membrane may be kept higher than gas pressure in a space facing the detection membrane. In this case, an increased amount of hydrogen gas leaks through a defect, enabling quicker detection of the defect.

The detection membrane may include, in addition to the thin film layer, a catalyst layer which is brought in contact with the ion-conductive electrolyte membrane, for example. In this case, the thin film layer varies in electric resistance by undergoing hydrogenation by hydrogen gas passing through the ion-conductive electrolyte membrane, under the catalytic action of the catalyst layer in contact with the ion-conductive electrolyte membrane. A defect can be found out by detecting such change in electric resistance.

Specifically, the thin film layer may be formed of a magnesium-nickel alloy, a magnesium-titanium alloy, a magnesium-niobium alloy, a magnesium-manganese alloy, a magnesium-cobalt alloy or magnesium, for example. The catalyst layer may be formed of palladium or platinum, for example. In this case, the thin film layer varies in electric resistance by hydrogenation, quickly and reversibly.

In order to achieve the above object, in another method for examining an ion-conductive electrolyte membrane according to the present invention, a first surface of the ion-conductive electrolyte membrane is divided into a plurality of regions. A detection membrane having thin film layers provided to correspond to those regions, respectively, is joined to the first surface of the ion-conductive electrolyte membrane, while a hydrogen electrode is joined to a second surface of the ion-conductive electrolyte membrane. In this state, an electric circuit is connected between the thin film layers and the hydrogen electrode for each of the regions, and hydrogen gas is supplied to a space facing the hydrogen electrode. At the hydrogen electrode, the hydrogen gas supplied is ionized. Electrons resulting from the ionization of the hydrogen gas are supplied from the hydrogen electrode to the thin film layers connected to the electric circuit, via the electric circuit. The hydrogen ions, on the other hand, are supplied from the hydrogen electrode to the ion-conductive electrolyte membrane, permeate through the ion-conductive electrolyte membrane and hydrogenate the thin film layers, where the thin film layers each vary in electric resistance to a degree depending on the amount of hydrogen ions permeating through the corresponding region of the ion-conductive electrolyte membrane.

Suppose that all the regions are equal in area and shape and that the catalyst layer as well as the thin film layers are uniform in chemical and electrical characteristics for all the regions. If the hydrogen ion conductivity of the ion-conductive electrolyte membrane is uniform in all the regions, all the thin film layers corresponding to the respective regions uniformly vary in electric resistance. Thus, by measuring the electric resistance of each of the thin film layers provided for the respective regions in the manner described above and examining whether or not the thin film layers have undergone a uniform change in electric resistance, it can be quickly determined whether or not the ion-conductive electrolyte membrane has uniform hydrogen ion conductivity. Incidentally, the above-described examination on the hydrogen ion conductivity can be conducted at normal temperatures.

This makes it possible to quickly sort out the ion-conductive electrolyte membranes or membrane electrode assemblies having uniform hydrogen ion conductivity. Application of such examination method to a fuel cell manufacturing process, for example, can simplify the manufacturing process and reduce the cost.

The electric circuit may be a power supply circuit, where a positive terminal of the power supply circuit is electrically connected to the hydrogen electrode, and a negative terminal of the power supply circuit is electrically connected to the thin film layers, for example. In this case, the electrons produced at the hydrogen electrode travel to the positive terminal of the power supply circuit and are supplied from the negative terminal to the thin film layers, while the electric field produced between the hydrogen electrode and the thin film layers increases the hydrogen ion conductivity of the ion-conductive electrolyte membrane. This enables better examination of the ion-conductive electrolyte membrane on uniformity of hydrogen ion conductivity.

The detection membrane may include, in addition to the thin film layers, a catalyst layer which is brought in contact with the ion-conductive electrolyte membrane. In this case, hydrogen ions permeating through the ion-conductive electrolyte membrane hydrogenate the thin film layers under the catalytic action of the catalyst layer, resulting in a change in electric resistance of the thin film layers. Thus, whether or not the ion-conductive electrolyte membrane has uniform hydrogen ion conductivity can be examined by detecting the electric resistance of the thin film layer in each region.

The hydrogen electrode may include a hydrogen diffusion membrane and an anode, where the anode is electrically connected to the positive terminal of the power supply circuit and brought in contact with the ion-conductive electrolyte membrane, for example. In this case, the hydrogen diffusion membrane diffuses hydrogen gas, resulting in efficient production of hydrogen ions at the anode.

Specifically, the thin film layers may be each formed of a magnesium-nickel alloy, a magnesium-titanium alloy, a magnesium-niobium alloy, a magnesium-manganese alloy, a magnesium-cobalt alloy or magnesium, for example. The catalyst layer, on the other hand, may be formed of palladium or platinum, for example. In this case, the thin film layers vary in electric resistance by hydrogenation, quickly and reversibly.

In order to achieve the above-mentioned object, an apparatus for examining an ion-conductive electrolyte membrane according to the present invention comprises a detection membrane having a plurality of thin film layers and joined to a first surface of the ion-conductive electrolyte membrane, and a hydrogen electrode joined to a second surface of the ion-conductive electrolyte membrane, wherein the apparatus further comprises a container providing a space facing the hydrogen electrode, an electric circuit selectively connected between the hydrogen electrode and each of the thin film layers arranged to correspond to a plurality of regions into which the first surface of the ion-conductive electrolyte membrane is divided, with a switch interposed, and an ohmmeter measuring electric resistance of each of the thin film layers.

In this examination apparatus, with the switch in "OFF" position, hydrogen gas is supplied to the space facing the hydrogen electrode, and electric resistance of each of the thin film layers is measured by the ohmmeter. If the ion-conductive electrolyte membrane has a defect, the thin film layer corresponding to the region with the defect is hydrogenated and varies in electric resistance. Thus, whether or not a defect exists can be examined by observing a change in electric resistance of each thin film layer.

Further, with the switch in "ON" position, hydrogen gas is supplied to the space facing the hydrogen electrode, and electric resistance of each of thin film layers connected to the electric circuit is measured by the ohmmeter. Here, by examining whether or not the electric resistances detected for each of the thin film layers are uniform, it can be examined whether or not the ion-conductive electrolyte membrane has uniform hydrogen ion conductivity.

Thus, this examination apparatus allows both the examination of the ion-conductive electrolyte membrane for defects and the examination of the ion-conductive electrolyte membrane on uniformity of hydrogen ion conductivity to be conducted in a continuous process only by operations such as operating the switch and supplying hydrogen gas. This makes it possible to conduct examination and sort out the ion-conductive electrolyte membranes or membrane electrode assemblies having no defect and being uniform in hydrogen ion conductivity, at reduced costs.

The electric circuit may be a power supply circuit, where a positive terminal of the power supply circuit is electrically connected to the hydrogen electrode, and a negative terminal of the power supply circuit is electrically connected to the thin film layers, for example. In this case, the electrons produced at the hydrogen electrode travel to the positive terminal of the power supply circuit and are supplied from the negative terminal to the thin film layers, while the electric field produced between the hydrogen electrode and the thin film layers increases the hydrogen ion conductivity of the ion-conductive electrolyte membrane. This enables better examination of the ion-conductive electrolyte membrane on uniformity of hydrogen ion conductivity.

The apparatus may further comprise a gas pressure regulation means for keeping gas pressure in the space facing the hydrogen electrode higher than gas pressure in a space facing the detection membrane. In this case, an increased amount of hydrogen gas leaks through a defect, enabling quicker detection of the defect.

BEST MODE OF CARRYING OUT THE INVENTION

Figure 1:
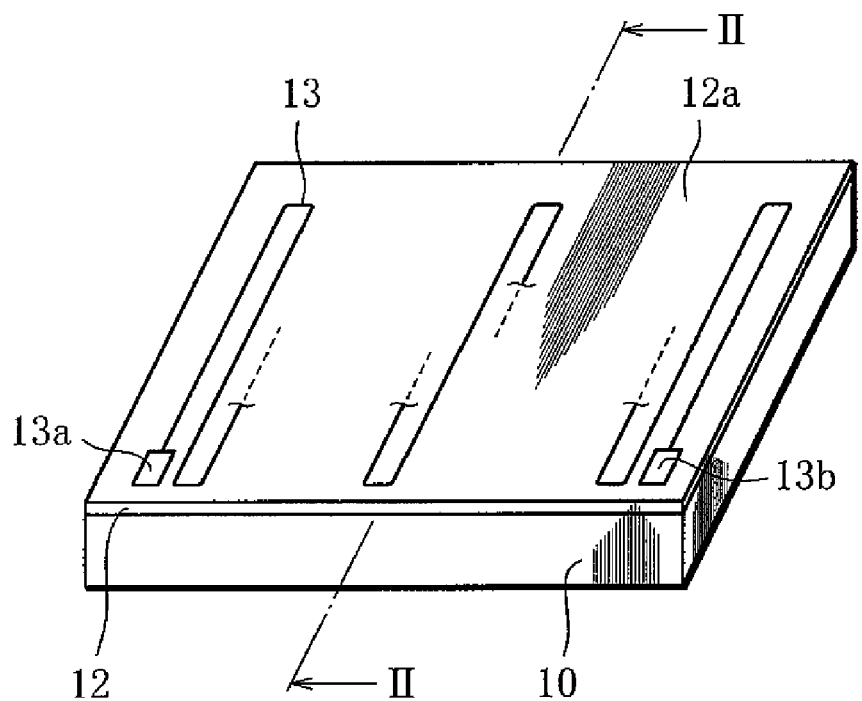
FIG. 1 is a perspective view showing an electrolyte membrane to be examined by an examination method according to a first embodiment of the present invention, and a detection membrane joined to the electrolyte membrane.

Referring to the drawings, methods and apparatuses for examining an ion-conductive electrolyte membrane according to embodiments of the present invention will be described in detail.

First, as a method for examining an ion-conductive electrolyte membrane according to a first embodiment of the present invention, a method for examining whether or not an ion-conductive electrolyte membrane has a defect, such as a pin hole or a crack, will be described with reference to FIGS. 1 to 3.

FIG. 1 is a perspective view showing an electrolyte membrane to be examined and a detection membrane joined to the electrolyte membrane. FIG. 2 is a cross-sectional view of the electrolyte membrane, etc. taken along line II-II in FIG. 1, and FIG. 3 is a schematic diagram showing an example of how the electrolyte membrane, etc. shown in FIG. 1 are arranged in a container to conduct examination.

Figure 2:
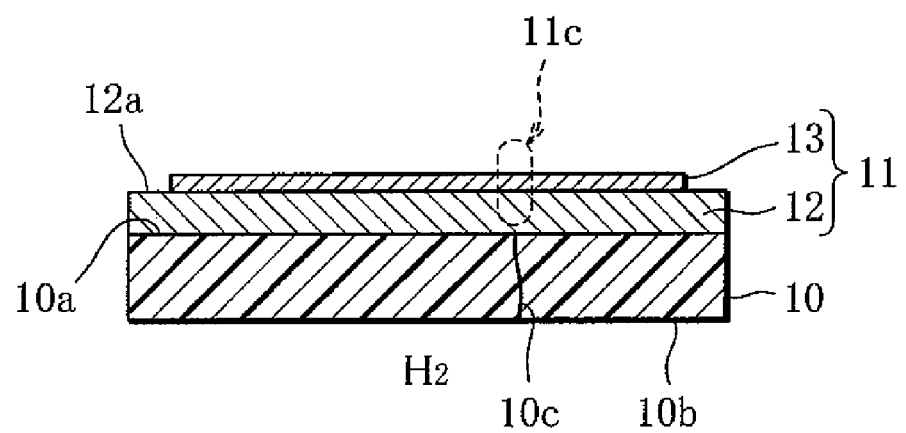
FIG. 2 is a schematic cross-sectional view taken along line II-II in FIG. 1.

As shown in FIGS. 1 and 2, a detection membrane 11, equal in planar shape to an electrolyte membrane 10, comprises a catalyst layer 12 and a thin film layer 13. The catalyst layer 12 is joined to a first surface 10a constituting one side of the electrolyte membrane 10, and the thin film layer 13 is formed on the surface of the catalyst layer 12. As shown in FIG. 1, the thin film layer 13 is in the shape of a line that extends meandering almost all over the surface 12a of the catalyst layer 12. An electrode 13a is formed at an end of the thin film layer 13, while an electrode 13b is formed at the other end thereof. Reference character 10b in FIG. 2 denotes a second surface constituting the other side of the electrolyte membrane 10. The electrolyte membrane 10 may be, for example a perfluorosulfonic group polymer membrane, a Nafion membrane or the like, each being a solid polymer membrane.

The thin film layer 13 is a thin film of elemental composition MgNi$_x$ ($0 \leq x < 0.6$), for example. Alternatively, the thin film layer 13 may be formed of a magnesium-titanium alloy, a magnesium-niobium alloy, a magnesium-manganese alloy, a magnesium-cobalt alloy or magnesium. The catalyst layer 12 is formed of palladium or platinum, for example, and 1 nm to 100 nm thick. When the detection membrane 11 described above is exposed to an atmosphere with a hydrogen concentration of about 100 ppm or more, the thin film layer 13 is quickly and reversibly hydrogenated, in ten ms or so, and thus quickly varies (increases) in electric resistance (hereinafter, sometimes referred to simply as "resistance").

Incidentally, if a thin film layer 13 and a catalyst layer 12 are formed on a polyethylene sheet in this order to form a detection membrane 11, it is easy to handle. In this case, the polyethylene sheet is on the top surface of the detection membrane 11 shown in FIGS. 1 and 2.

Figure 3:
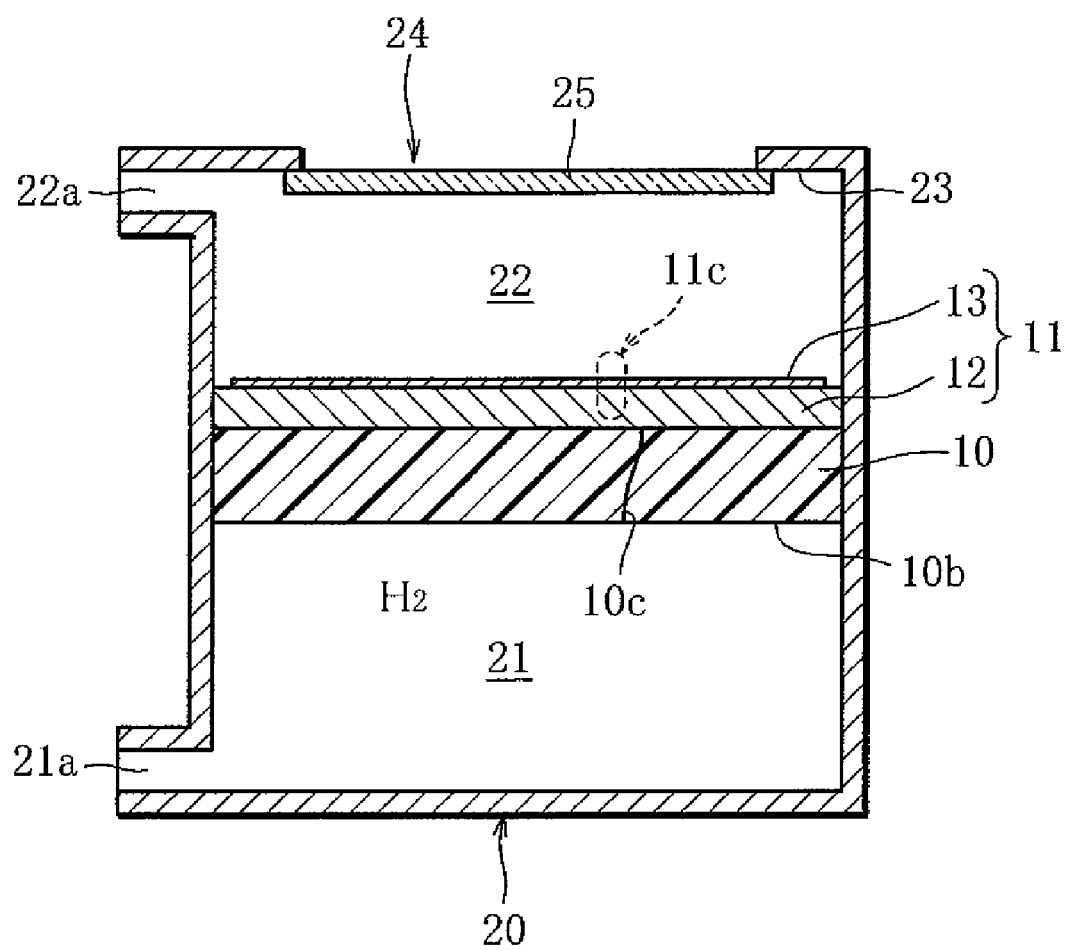
FIG. 3 is a diagram showing an example of how an electrolyte membrane, etc. are arranged in a container in order to examine the electrolyte membrane for defects, by the examination method according to the first embodiment of the present invention.

In examination of the electrolyte membrane 10, the electrolyte membrane 10 with the detection membrane 11 joined is arranged in a container 20 as shown in FIG. 3, and then hydrogen gas ($H_2$) is supplied to a first space 21 facing the second surface 10b of the electrolyte membrane 10, through a first supply port 21a, by a pump not shown. To a second space 22 facing the detection membrane 11, gas containing little hydrogen gas (air, for example) is supplied, through an air supply port 22a of the container 20, by a pump not shown. The first space 21 and the second space 22 are separated by the electrolyte membrane 10. Here, it is preferable to keep the gas pressure in the first space 21 higher than the gas pressure in the second space 22. Incidentally, a window 24 is provided in a wall 23 surrounding the second space 22 to allow transfer of the electrolyte membrane 10 into and from the container 20, etc. The window 24 is closed with a glass panel 25. The electrolyte membrane 10 with the detection membrane 11 joined is fixed in place inside the container 20, by means of a frame (not shown) surrounding it, for example.

When the electrolyte membrane 10 does not have a defect such as a pin hole, hydrogen gas supplied to the first space 21 is prevented from contacting the detection membrane 11 by the electrolyte membrane 10. Consequently, the detection membrane 11 is not hydrogenated, so that the resistance between the electrodes 13a and 13b of the thin film layer 13 (hereinafter, sometimes referred to as "resistance of the thin film layer 13") does not vary.

When the electrolyte membrane 10 has a crack 10c (defect), on the other hand, hydrogen gas leaks from the second surface 10b side to the first surface 10a side of the electrolyte membrane 10 through the crack 10c. Consequently, the thin film layer 13 is hydrogenated in a region 11c of the detection membrane 11 near the crack 10c, to a degree depending on the amount of leaked hydrogen gas, resulting in a quick change in resistance of the thin film layer 13. Even if the crack 10c is not right under the thin film layer 13, leaked hydrogen gas diffuses near the crack 10c and causes a change in resistance in some portion of the thin film layer 13 extending almost all over the surface 12a of the catalyst layer 12. In other words, if the value of resistance of the thin film layer 13 after the supply of hydrogen gas to the first space 21 is different from that before the supply, it can be inferred that the thin film layer 13 has been hydrogenated by the hydrogen gas that has leaked owing to a defect of the electrolyte membrane 10, and therefore it can be determined that the electrolyte membrane 10 has a defect such as a pin hole.

The joining of the detection membrane 11 to the first surface 10a of the electrolyte membrane 10 does not need to create a perfectly tight contact leaving no space between them at all. The reason is that even if both membranes are joined together with a slight space between them, hydrogen gas leaking through the crack 10c can hydrogenate the thin film layer 13 in a portion nearest to the crack 10c.

In examination of a hydrogen ion-conductive electrolyte membrane, the electrolyte membrane 10 may have a hydrogen electrode joined to the second surface 10b. The reason is that if the electrolyte membrane 10 has a defect, hydrogen gas permeates through the hydrogen electrode, then leaks through the defect to the first surface 10a of the electrolyte membrane 10 and hydrogenates the thin film layer 13. Thus, a semifinished electrode membrane assembly with a hydrogen electrode joined to a hydrogen ion-conductive electrolyte membrane can be examined for defects. Further, the hydrogen electrode joined adds its thickness to the assembly consisting of the detection membrane 11 and the electrolyte membrane 10 joined together (the membranes are each very thin), thereby making the electrolyte membrane 10, etc. easy to handle.

The shape of the electrolyte membrane is not restricted to a flat plate as in the present embodiment; It may be in another planar shape. If the electrolyte membrane is in the shape of a tube, the examination may be conducted by joining a detection membrane onto the outer cylindrical surface of the tubular electrolyte membrane and supplying hydrogen gas to the space inside the tube, for example.

Figure 5:
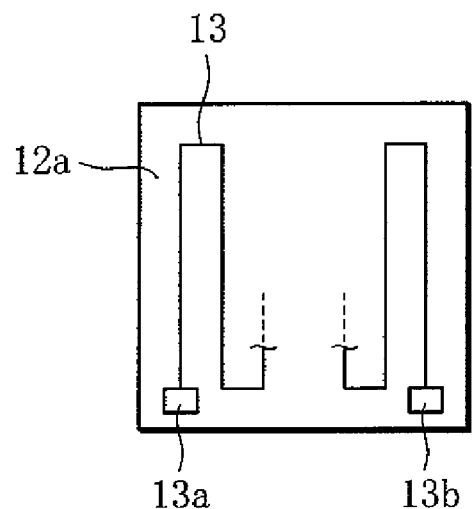
FIG. 5 is a plan view showing a schematic arrangement of a thin film layer, etc. for one region of the electrolyte membrane of FIG. 4.
Figure 6:
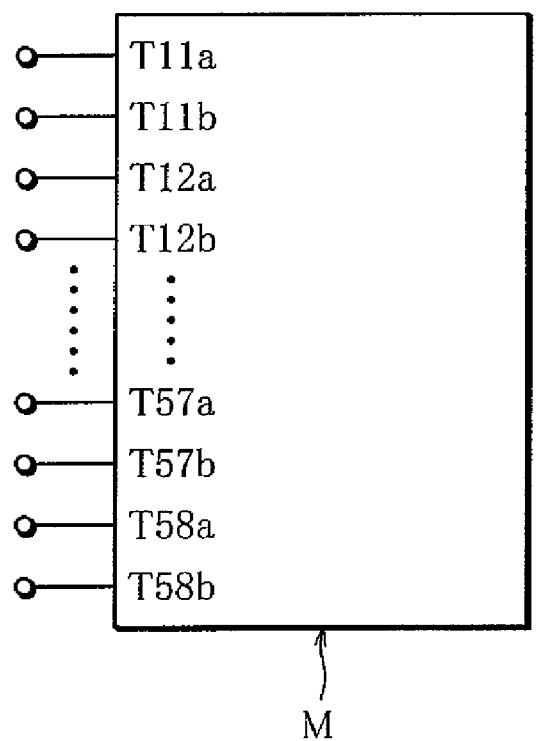
FIG. 6 is a diagram showing an example of an ohmmeter for measuring resistance of thin film layers arranged to correspond to the respective regions of the electrolyte membrane of FIG. 4.

Next, as a method for examining an ion-conductive electrolyte membrane according to a second embodiment of the present invention, a method for identifying a portion of an ion-conductive electrolyte membrane having a defect will be described with reference to FIGS. 4 to 6. The components similar in function to those in the first embodiment will be assigned the same reference characters and the description thereof will be omitted.

Figure 4:
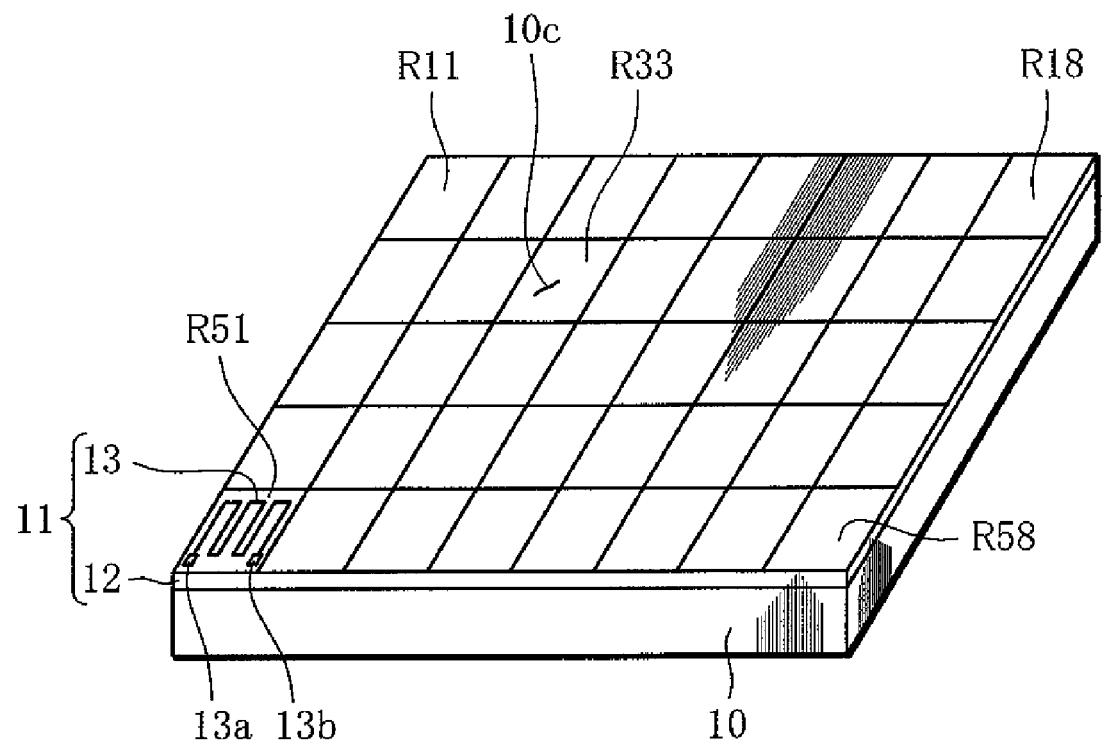
FIG. 4 is a perspective view showing an electrolyte membrane to be examined by an examination method according to a second embodiment of the present invention, and a detection membrane joined to the electrolyte membrane.

As shown in FIG. 4, a first surface 10a constituting one side of an electrolyte membrane 10 is divided laterally into 8 and vertically into 5, thus into 40 regions (equal square regions). For each of surface regions (regions R11 to R58) of a detection membrane 11 corresponding to these regions, a thin film layer 13 is formed with electrodes 13a and 13b, as shown in FIG. 5.

The thin film layers 13 in the respective regions are equal in elemental composition, shape, etc., and therefore uniform in chemical and electrical characteristics. The thin film layers 13 in the regions R11 to R58 are electrically connected to an ohmmeter M shown in FIG. 6. The ohmmeter M has terminals 11a to 58a and terminals 11b to 58b, corresponding to the regions R11 to R58. The terminals 11a and 11b form a pair and are electrically connected to the electrodes 13a and 13b in the region R11, respectively. Also with respect to the other terminals, the terminals having the same number but different subscripts "a" and "b" (terminals T12a and T12b, for example) form a pair and are electrically connected to the electrodes 13a and 13b in the region having the same number, among the regions R12 to R58, respectively, like the paired terminals T11a and T11b.

The ohmmeter M undergoes program control and measures and records values of resistance of the thin film layers 13 in the respective regions at predetermined intervals. Under the program control, the ohmmeter M not only detects a change in resistance of the thin film layer 13 in each region, but also determines whether or not the values of resistance of the thin film layers in the respective regions are within a predetermined allowable range of uniformity. When determining that the resistance values of the thin film layers 13 in the respective regions are not uniform, the ohmmeter M determines in which region the resistance value of the thin film layer 13 is different from those in the other regions.

The method for examining the electrolyte membrane 10 using the ohmmeter M is specifically as follows: The detection membrane 11 is joined to the first surface 10a of the electrolyte membrane 10, and the electrolyte membrane 10 with the detection membrane 11 joined is arranged in a container 20 as in the first embodiment. Then, with hydrogen gas ($H_2$) being supplied to the first space 21, the ohmmeter M measures the resistance of the thin film layer 13 in each region.

If the electrolyte membrane 10 has no defects such as pin holes, hydrogen gas supplied to the first space 21 is prevented from contacting the detection membrane 11 by the electrolyte membrane 10. Thus, the detection membrane 11 is not hydrogenated and the resistance of the thin film layer 13 does not vary in any of the regions R11 to R58. In this case, the ohmmeter M determines that the electrolyte membrane 10 has no defect.

If, on the other hand, the electrolyte membrane 10 has a crack 10c in a region corresponding to the region R33 as shown in FIG. 4, for example, hydrogen gas leaks from the second surface 10b side to the first surface 10a of the electrolyte membrane 10 through the crack 10c. Consequently, under the catalytic action of the catalyst layer 12, the resistance of the thin film layer 13 in the region R33 near the crack 10c varies. At this time, finding that the resistance value in the region R33 is different from that in the other regions, the ohmmeter M determines that there exists a defect in the region corresponding to the region R33.

Also when a defect exists in a region other than the region corresponding to the region R33 or when more than one region have a defect, the ohmmeter M can identify such region(s) having a defect in the same way.

Next, as a method for examining an ion-conductive electrolyte membrane according to a third embodiment of the present invention, a method for examining an ion-conductive electrolyte membrane on hydrogen ion conductivity will be described with reference to FIGS. 7 to 11.

Figure 7:
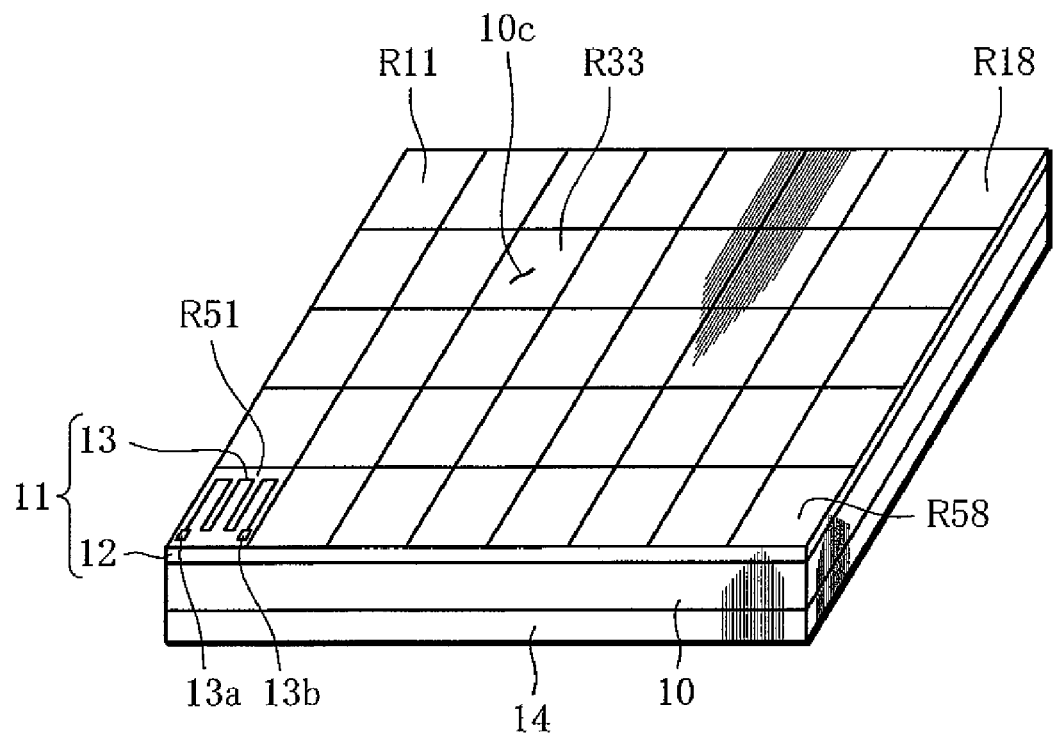
FIG. 7 is a perspective view showing an electrolyte membrane to be examined by an examination method according to a third embodiment of the present invention, with a detection membrane and a hydrogen electrode each joined to the electrolyte membrane.
Figure 8:
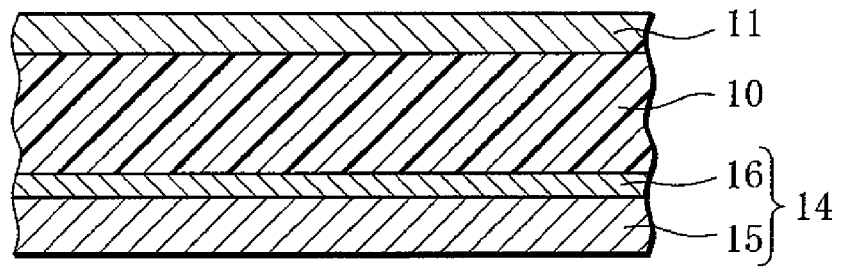
FIG. 8 is a schematic cross-sectional view showing the electrolyte membrane, detection membrane and hydrogen electrode of FIG. 7.
Figure 9:
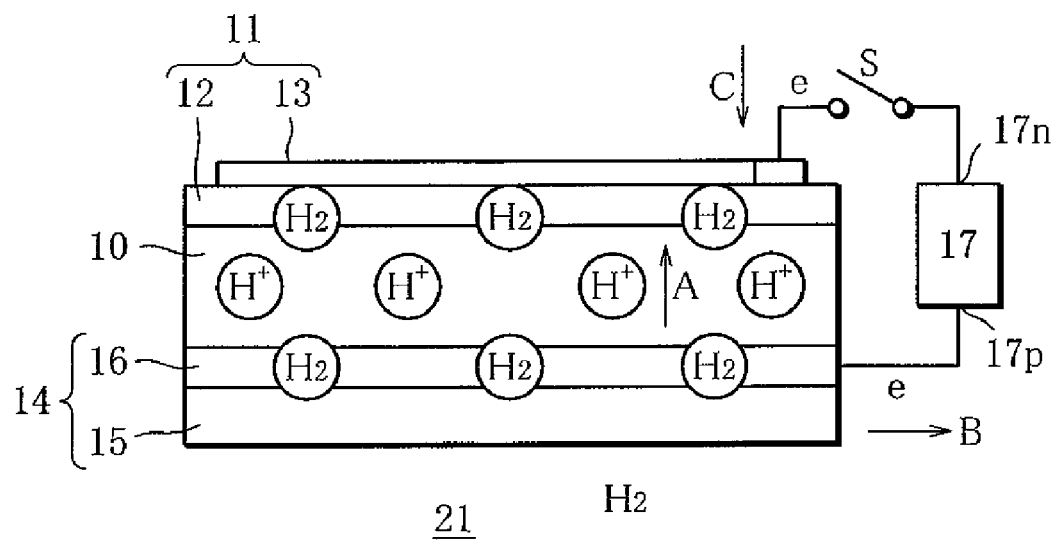
FIG. 9 is a schematic diagram showing a circuit structure for examining the electrolyte membrane of FIG. 7 on hydrogen ion conductivity, and also giving an explanation of hydrogen ion conductivity of the electrolyte membrane.
Figure 10:
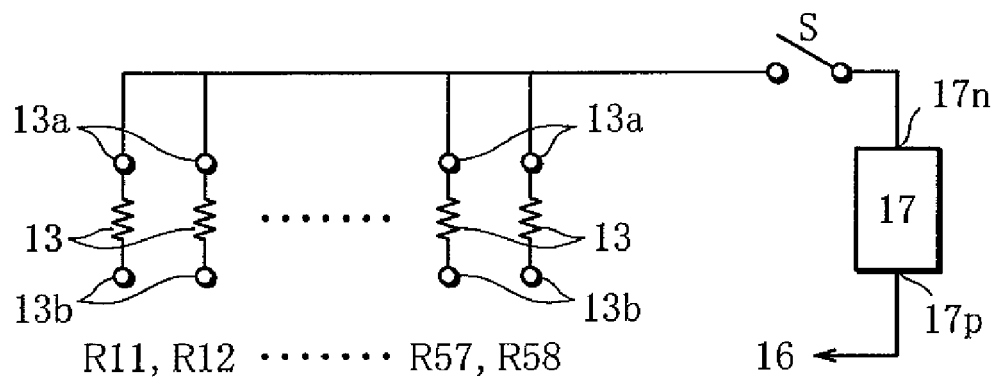
FIG. 10 is a diagram showing how the resistance of thin film layers is measured by the circuit of FIG. 9.
Figure 11:
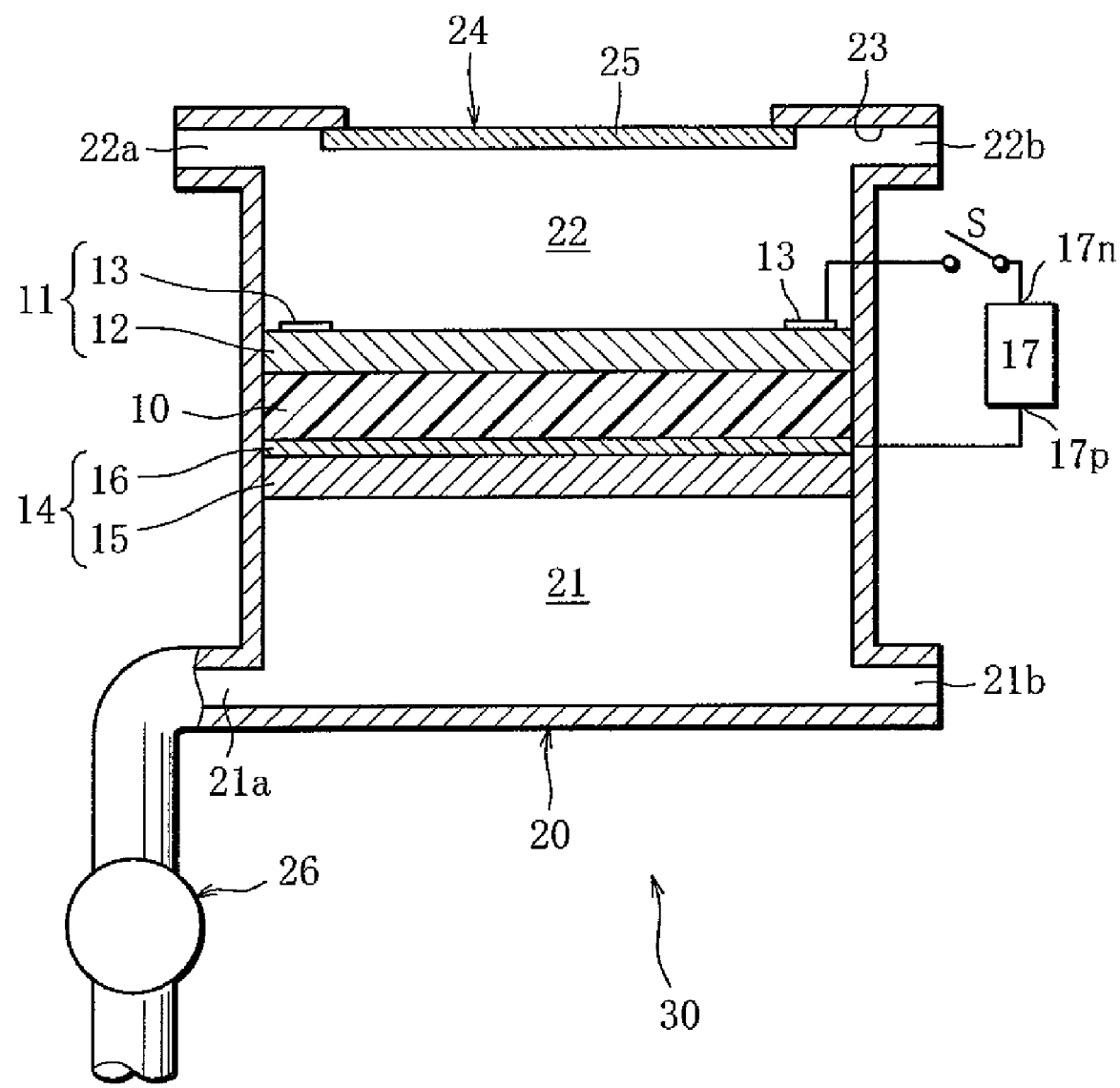
FIG. 11 is a schematic structural diagram showing an example of how an electrolyte membrane, etc. are arranged in a container in order to examine the electrolyte membrane on hydrogen ion conductivity by the examination method according to the third embodiment of the present invention, and an examination apparatus according to a fourth embodiment of the present invention.

FIG. 7 is a perspective view showing an electrolyte membrane to be examined, with a detection membrane and a hydrogen electrode each joined to the electrolyte membrane. FIG. 8 is a schematic cross-sectional view showing the electrolyte membrane, hydrogen electrode and detection membrane. FIG. 9 is a schematic diagram showing a circuit structure for examining the electrolyte membrane on hydrogen ion conductivity, and also giving an explanation of the hydrogen ion conductivity of the electrolyte membrane. FIG. 10 is a schematic diagram showing how the resistance of thin film layers is measured by such circuit. FIG. 11 is a schematic diagram showing an example of how an electrolyte membrane, etc. are arranged in a container in order to examine the electrolyte membrane on hydrogen ion conductivity by the examination method according to the third embodiment. The components similar in function to those in the above-described first and second embodiments will be assigned the same reference characters and the description thereof will be omitted.

As shown in FIG. 7, an electrolyte membrane 10 is divided into regions corresponding to regions R11 to R58 as in the above-described second embodiment. To a first surface 10a constituting one side of the electrolyte membrane 10, a detection membrane 11 equal in planar shape to the electrolyte membrane 10 is joined. For each of surface regions (regions R11 to R58) of the detection membrane 11 corresponding to the respective regions of the electrolyte membrane 10, a thin film layer 13 is formed with electrodes 13a, 13b, as in the second embodiment. As shown in FIGS. 7 and 8, a hydrogen electrode 14, equal in planar shape to the electrolyte membrane 10, comprises a hydrogen diffusion membrane 15 and an anode 16, where the anode 16 is joined to a second surface 10b constituting the other side of the electrolyte membrane 10. Thus, the detection membrane 11 and the hydrogen electrode 14 face each other with the electrolyte membrane 10 interposed between them.

The hydrogen diffusion membrane 15 of the hydrogen electrode 14 is formed of carbon fibers, such as carbon paper or carbon cloth, or porous resin, porous ceramic, porous metal (foamed metal) or the like, for example. The thickness of the hydrogen diffusion membrane 15 is 0.1 mm to 50 mm, for example. The anode 16 is a membrane formed of a hydrogen ionization catalyst such as platinum, for example.

The hydrogen electrode 14 may be provided either as a component which constitutes, together with the electrolyte membrane 10, part of a membrane electrode assembly for a fuel cell, or as a member exclusively for examination which is temporarily joined to the electrolyte membrane 10 in examination.

As shown in FIG. 9, the anode 16 of the hydrogen electrode 14 is connected to a positive terminal 17p of a power supply circuit 17, while the electrode 13a of the thin film layer 13 is connected to a negative terminal 17n of the power supply circuit 17 with a switch S interposed between them. Thus, the power supply circuit 17 constitutes part of an electric circuit passing electrons from the anode 16 to the thin film layer 13, and can cause the thin film layer 13 to have a negative potential with respect to the anode 16, thereby producing an electric field between the thin film layer 13 and the anode 16.

In the examination of the electrolyte membrane 10 on hydrogen ion conductivity, the electrolyte membrane 10 with the hydrogen electrode 14 and the detection membrane 11 joined is arranged in the container 20 as shown in FIG. 11. To a first space 21 inside the container 20 facing the hydrogen electrode 14, hydrogen gas ($H_2$) is supplied through a first supply port 21a. To a second space 22 facing the detection membrane 11, air (or oxygen) is supplied through an air supply port 22a. Naturally, both spaces are separated by the electrolyte membrane 10, etc. In FIG. 11, reference character 21b denotes a collection port for collecting unreacted hydrogen gas, and reference character 22b denotes a discharge port for discharging unreacted air (or oxygen) and water vapor produced at the detection membrane 11. It is preferable to keep the gas pressure in the first space 21 higher than the gas pressure in the second space 22 by a pump (gas pressure regulation means) 26. Such pressurizing by the pump 26 allows easier passage of hydrogen gas through the hydrogen electrode 14.

As shown in FIG. 9, hydrogen gas ($H_2$) supplied to the first space 21 is diffused through the hydrogen diffusion membrane 15 to reach the anode 16. At the anode 16, the hydrogen gas ($H_2$) is split into hydrogen ions ($H^+$) and electrons (e). With the switch S in "ON" position, the hydrogen ions ($H^+$) permeate through the electrolyte membrane 10 to reach the catalyst layer 12 as indicated by arrow A in the Figure, owing to electrical repulsive force generated by the positive potential of the power supply circuit and electrical attractive force generated by the negative potential given to the thin film layer 13 with respect to the anode 16. The electrons (e), on the other hand, travel from the positive terminal 17p to the negative terminal 17n of the power supply circuit 17, and then to the thin film layer 13 of the detection membrane 11 and further to the catalyst layer 12 as indicated by arrows B and C in the Figure. The hydrogen ions ($H^+$) permeating through the electrolyte membrane 10 combine with the electrons (e) to form hydrogen gas ($H_2$) near the interface between the electrolyte membrane 10 and the catalyst layer 12. The hydrogen gas ($H_2$) thus formed reacts with the thin film layer 13 under the action of the catalyst layer 12, or in other words, hydrogenates the thin film layer 13 reversibly. Here, the degree of hydrogenation of the thin film layer 13 depends on the amount of hydrogen ions ($H^+$) arriving at the detection membrane 11. Incidentally, the switch S may be put into "ON" position either after or before hydrogen gas ($H_2$) is supplied to the first space 21. To sum up, what is required is putting the switch S into "ON" position so that hydrogen ions ($H^+$) will permeate through the electrolyte membrane 10.

If the hydrogen ion conductivity of the electrolyte membrane 10 is uniform in the regions corresponding to the regions R11 to R58, the amount of hydrogen ions ($H^+$) arriving at the catalyst layer 12 is equal in these regions. Thus, an ohmmeter M measures the resistance of the thin film layer 13 in each region, and determines whether or not the values of resistance of the thin film layers in the respective regions are within a predetermined allowable range of uniformity. In this manner, it can be determined whether or not every region of the electrolyte membrane 10 has hydrogen ion conductivity within a uniformity range allowable from the viewpoint of quality assurance, for example. If the hydrogen ion conductivity of the electrolyte membrane 10 is not uniform, the resistance value of a thin film layer 13 in a region of the detection membrane 11 contacting a region of the electrolyte membrane having lower hydrogen ion conductivity is different from the resistance value in the other regions. Thus, the ohmmeter M can not only determine whether or not the hydrogen ion conductivity of the electrolyte membrane 10 is uniform, but also identify a region having lower hydrogen ion conductivity.

The joining of the detection membrane 11 to the first surface 10a of the electrolyte membrane 10 does not need to create a perfectly tight contact leaving no space between them at all. This applies also to the joining of the hydrogen electrode 14 to the second surface 10b of the electrolyte membrane 10. The reason is that even if both or either of these connections include a slight space, the electric field produced between the thin film layers 13 and the anode 16 causes the hydrogen ions ($H^+$) produced at the anode 16 to permeate through the electrolyte membrane 10 and move straight to the detection membrane 11.

If the hydrogen electrode 14 constitutes part of a membrane electrode assembly for a fuel cell, together with the electrolyte membrane 10, the membrane electrode assembly with the hydrogen electrode 14 joined to the electrode membrane 14 can be subjected to the examination on hydrogen ion conductivity.

The resistance of the thin film layers 13 in the regions R11 to R58 can be measured, with the electrode 13a of each thin film layer 13 connected to the negative terminal 17n of the power supply circuit 17 as shown in FIG. 10, for example. In other words, the ohmmeter M can measure the resistance of each thin film layer 13, while hydrogen ions (H+) are caused to be permeating through the electrolyte membrane 10 by the power supply circuit 17 connected. Here, the electrons (e) traveling through each thin film layer 13 produce a potential difference between the electrodes 13a and 13b of each thin film layer 13. If the hydrogen ion conductivity is uniform in the regions corresponding to the regions R11 to R58, the potential difference between the electrodes 13a and 13b of the thin film layer 13 is equal in these regions. Thus, the ohmmeter M can detects a difference in resistance in the thin film layers 13, on the basis of potential difference between the electrodes 13a and 13b of each thin film layer 13.

Next, as a method and apparatus for examining an ion-conductive electrolyte membrane according to a fourth embodiment of the present invention, an examination method and apparatus capable of conducting examination of an ion-conductive electrolyte membrane for defects and examination thereof on hydrogen ion conductivity in a continuous process will be described with reference to the drawings referred to in the explanation of the above embodiments.

As shown in FIG. 11, an examination apparatus 30 according to this embodiment is similar in structure to the third embodiment, and examines an electrolyte membrane 10 as shown in FIGS. 7 and 8. Specifically, the examination apparatus 30 has a first space 21 (facing a hydrogen electrode) 21 defined inside a container 20 and a second space 22 opposite to the first space 21 with respect to the electrolyte membrane 10, inside the container 20. The examination apparatus 30 further includes a power supply circuit 17, a switch S and an ohmmeter M. With the switch in "OFF" position, the examination apparatus 30 can examine the electrolyte membrane 10 for defects, by the procedure described with respect to the second embodiment. Further, with the switch in "ON" position, it can examine the electrolyte membrane 10 on hydrogen ion conductivity, by the procedure described with respect to the third embodiment.

Here, if a defect is detected in the defect examination of the electrolyte membrane 10 with the examination apparatus 30, it can be determined that the electrolyte membrane 10 does not have desired quality, without conducting examination on uniformity of hydrogen ion conductivity. By conducting the above-described examination on uniformity of hydrogen ion conductivity on those electrolyte membranes 10 which have passed the defect examination, electrolyte membranes 10 having no defect and being uniform in hydrogen ion conductivity can be sorted out.

In other words, the examination apparatus 30 can discover electrolyte membranes 10 not having desired quality in the preceding defect examination, and therefore save the examination on uniformity of hydrogen ion conductivity for such defective electrolyte membranes 10. Thus, the examination apparatus 30 can not only shorten the examination time because of its continuous examination process, but also further shorten the examination time because it cuts the time consumed in wasteful examination. It goes without saying that also when the examination on uniformity of hydrogen ion conductivity is conducted before the defect examination, the examination time can be reduced likewise. In this case, the examination on hydrogen ion conductivity results in hydrogenation of the thin film layers 13 joined to the electrolyte membrane 10. Thus, prior to the defect examination, the thin film layers 13 joined to the electrolyte membrane 10 are brought back to the state before hydrogenation, by stopping supply of hydrogen gas to the first space 21 and supplying air or the like to the second space 22. The examination apparatus 30 can thus simplify the process of examining the electrolyte membrane 10 and shorten the examination time.

The present invention is not restricted to the above-described embodiments, but can be modified appropriately without departing from the scope and spirit of the invention.

The invention claimed is:

1. A method for examining an ion-conductive electrolyte membrane, comprising the steps of:
   joining a detection membrane including a thin film layer to a first surface of the ion-conductive electrolyte membrane;
   supplying hydrogen gas to a space facing a second surface of the ion-conductive electrolyte membrane; and
   measuring an electrical resistance of the thin film layer; and
   determining that the ion-conductive electrolyte membrane has a defect when a change in the electrical resistance of the thin film layer is caused by hydrogenation of the thin film layer due to hydrogen gas leaking from the second surface to the first surface through the defect.

2. The method for examining the ion-conductive electrolyte membrane according to claim 1, wherein the thin film layer is provided for each of a plurality of regions into which the first surface of the ion-conductive electrolyte membrane is divided, and the step of determining whether the ion-conductive electrolyte membrane has a defect includes a step of determining that a defect exists in a region corresponding to a thin film layer having a change in electrical resistance.

3. The method for examining the ion-conductive electrolyte membrane according to claim 1, wherein gas pressure in the space facing the second surface of the ion-conductive electrolyte membrane is kept higher than gas pressure in a space facing the detection membrane.

4. The method for examining the ion-conductive electrolyte membrane according to claim 1, wherein the detection membrane includes the thin film layer and a catalyst layer brought in contact with the ion-conductive electrolyte membrane, and whether the ion-conductive electrolyte membrane has a defect is determined by observing the change in the electrical resistance of the thin film layer, which arises when the ion-conductive electrolyte membrane has the defect and the thin film layer is hydrogenated by hydrogen gas passing through the defect under catalytic action of the catalyst layer.

5. The method for examining the ion-conductive electrolyte membrane according to claim 4, wherein the thin film layer is formed of a magnesium-nickel alloy, a magnesium-titanium alloy, a magnesium-niobium alloy, a magnesium-manganese alloy, a magnesium-cobalt alloy or magnesium, and the catalyst layer is formed of palladium or platinum.

6. A method for examining an ion-conductive electrolyte membrane, comprising the steps of:
   dividing a first surface of the ion-conductive electrolyte membrane into a plurality of regions; joining a detection membrane having thin film layers provided to correspond to the regions, respectively, to the first surface of the ion-conductive electrolyte membrane;
   joining a hydrogen electrode to a second surface of the ion-conductive electrolyte membrane;
   connecting an electric circuit between the thin film layers and the hydrogen electrode for each of the regions;

supplying hydrogen gas to a space facing the hydrogen electrode to ionize the hydrogen gas at the hydrogen electrode;

supplying electrons resulting from the ionization from the hydrogen electrode to the thin film layers connected to the electric circuit, via the electric circuit, while supplying hydrogen ions resulting from the ionization from the hydrogen electrode to the ion-conductive electrolyte membrane to permeate through the ion-conductive electrolyte membrane;

detecting an electrical resistance of the thin film layer hydrogenated by the hydrogen ions permeating through the ion-conductive electrolyte membrane for each of the regions; and determining whether the ion-conductive electrolyte membrane has uniform hydrogen ion conductivity, depending on whether electrical resistances of the thin film layers, detected for each of the regions, are uniform.

7. The method for examining the ion-conductive electrolyte membrane according to claim 6, wherein the electric circuit is a power supply circuit, and a positive terminal of the power supply circuit is electrically connected to the hydrogen electrode while a negative terminal of the power supply circuit is electrically connected to the thin film layers.

8. The method for examining the ion-conductive electrolyte membrane according to claim 7, wherein the hydrogen electrode includes a hydrogen diffusion membrane and an anode, and the anode is electrically connected to the positive terminal of the power supply circuit and brought in contact with the ion-conductive electrolyte membrane.

9. The method for examining the ion-conductive electrolyte membrane according to claim 7, wherein the detection membrane includes the thin film layers and a catalyst layer brought in contact with the ion-conductive electrolyte membrane, and the step of detecting the electrical resistance of the thin film layer for each of the regions includes a step of detecting a change in the electrical resistance of the thin film layer for each of the regions, which results from hydrogenation of the corresponding thin film layer under catalytic action of the catalyst layer by hydrogen ions permeating through the ion-conductive electrolyte membrane.

10. The method for examining the ion-conductive electrolyte membrane according to claim 9, wherein the thin film layers are each formed of a magnesium-nickel alloy, a magnesium-titanium alloy, a magnesium-niobium alloy, a magnesium-manganese alloy, a magnesium-cobalt alloy or magnesium, and the catalyst layer is formed of palladium or platinum.

11. An apparatus for examining an ion-conductive electrolyte membrane, comprising a detection membrane having a plurality of thin film layers and joined to a first surface of the ion-conductive electrolyte membrane, and a hydrogen electrode joined to a second surface of the ion-conductive electrolyte membrane, the apparatus further comprising:

a container which provides a space facing the hydrogen electrode;

an electric circuit which is selectively connected between the hydrogen electrode and each of the thin film layers arranged to correspond to a plurality of regions into which the first surface of the ion-conductive electrolyte membrane is divided, with a switch interposed; and an ohmmeter for measuring electric resistance of each of the thin film layers;

wherein whether the ion-conductive electrolyte membrane has a defect is examined by the steps of:
supplying hydrogen gas to the space facing the hydrogen electrode, with the switch in an "OFF" position;
measuring an electrical resistance of each of the thin film layers by the ohmmeter; and
examining whether a change in the measured electrical resistance of each thin film layer is caused; and wherein whether the ion-conductive electrolyte membrane has uniform hydrogen ion conductivity is examined by the steps of:
supplying hydrogen gas to the space facing the hydrogen electrode, with the switch in an "ON" position;
measuring the electrical resistance of each of the thin film layers connected to the electric circuit by the ohmmeter; and
examining whether the electrical resistances detected for each of the thin film layers are uniform.

12. The apparatus for examining the ion-conductive electrolyte membrane according to claim 11, wherein the electric circuit is a power supply circuit, and a positive terminal of the power supply circuit is electrically connected to the hydrogen electrode while a negative terminal of the power supply circuit is electrically connected to the thin film layers.

13. The apparatus for examining the ion-conductive electrolyte membrane according to claim 11, further comprising a gas pressure regulation means for keeping gas pressure in the space facing the hydrogen electrode higher than gas pressure in a space facing the detection membrane.

* * * * *